United States Patent [19]

Sakai et al.

[11] Patent Number: 5,406,371
[45] Date of Patent: Apr. 11, 1995

[54] APPARATUS FOR MEASURING BIREFRINGENCE AND RETARDATION

[75] Inventors: Kiyokazu Sakai, Nishinomiya; Shinichi Nagata, Matsubara; Osamu Tomita, Osaka; Yo Tajima, Ashiya, all of Japan

[73] Assignee: New Oji Paper Co., Ltd., Tokyo, Japan

[21] Appl. No.: 918,761

[22] Filed: Jul. 27, 1992

[30] Foreign Application Priority Data

Jul. 29, 1991 [JP] Japan .................................. 3-188934

[51] Int. Cl.⁶ .............................................. G01J 4/00
[52] U.S. Cl. .................................... 356/367; 356/364; 356/365
[58] Field of Search ................ 356/364, 365, 366, 367, 356/368

[56] References Cited

U.S. PATENT DOCUMENTS

| | | | |
|---|---|---|---|
| 3,177,761 | 4/1965 | Redner | 356/366 |
| 4,146,332 | 3/1979 | Moore | 356/326 |
| 4,259,014 | 3/1981 | Talmi | 356/328 |
| 4,494,872 | 1/1985 | Busch | 356/328 |
| 4,568,187 | 2/1986 | Kita et al. | 356/328 |
| 4,575,241 | 3/1986 | Demers et al. | 356/328 X |
| 4,591,267 | 5/1986 | Demers et al. | 356/316 |
| 4,647,207 | 3/1987 | Björk et al. | 356/243 X |
| 4,690,559 | 9/1987 | Florek et al. | 356/328 |
| 4,940,325 | 7/1990 | Becker-Ross et al. | 356/307 X |
| 4,948,255 | 8/1990 | Watanabe | 356/367 |
| 4,973,163 | 11/1990 | Sakai et al. | 356/367 |
| 5,046,850 | 9/1991 | Tomoff | 356/367 |
| 5,166,752 | 11/1992 | Spanier et al. | 356/367 X |

*Primary Examiner*—Donald E. Czaja
*Assistant Examiner*—Milton I. Cano
*Attorney, Agent, or Firm*—William L. Klima

[57] ABSTRACT

In order to efficiently obtain data for calculating retardation values at a plurality of wavelengths, a sample having birefringence is placed between a polarizer and an analyzer, which are maintained in a parallel nicol relation to each other and rotated about an optical axis of measuring light. White measuring light is applied through the polarizer so that the light being passed through the sample and transmitted through the analyzer is received by a polychromator. A one-dimensional optical sensor is arranged on an outgoing imaging surface of the polychromator, to simultaneously detect transmitted light intensity values of a plurality of wavelengths. Since transmitted light intensity values of a plurality of wavelengths are obtained every polarization rotation angle of the polarizer and the analyzer, it is possible to obtain dispersion of retardation values with respect to wavelengths and the like by processing the data.

4 Claims, 5 Drawing Sheets

APPARATUS FOR MEASURING BIREFRINGENCE AND RETARDATION

BACKGROUND OF THE INVENTION

Field of the Invention

The present invention relates to an apparatus for measuring birefringence and retardation values of various film materials, and more particularly, it relates to a measuring apparatus which can obtain dispersion of retardation values with respect to wavelengths of measuring light.

Description of the Background Art

In a conventional retardation measuring apparatus, a sample to be measured is held between a polarizer and an analyzer which are maintained in a constant relation of polarization directions such as a parallel nicol relation, for example. Then monochromatic light is applied through the sample from the polarizer to measure intensity of the light being passed through the sample and transmitted through the analyzer, while relatively rotating the polarizer and the analyzer, maintained in the constant relation. Thus measured is dependency of the transmitted light intensity on the angle of rotation, thereby obtaining the retardation value with respect to the measuring light of the current wavelength.

In the conventional measuring apparatus, the sample or the combination of the polarizer and the analyzer is thus rotated in order to observe angle dependency of the transmitted light intensity. Therefore, it takes minutes to collect data required for obtaining a retardation value on a single point of the sample. Further, obtained through single measurement is only a retardation value at a specific wavelength as selected. In order to obtain a retardation value at another wavelength, it is necessary to change the wavelength of the measuring light as well as to newly rotate the sample or the combination of the polarizer and the analyzer again for collecting angle dependency data of the transmitted light intensity. Thus, a considerably long time is required also for collecting data for obtaining retardation values at a few wavelengths. Due to such a problem, data collection at a large number of wavelengths for obtaining dispersion of retardation values with respect to the wavelengths requires a great effort.

SUMMARY OF THE INVENTION

A first object of the present invention is to provide a birefringence measuring apparatus which can efficiently collect birefringence measurement data required for obtaining retardation values at a plurality of wavelengths.

A second object of the present invention is to provide a retardation measuring apparatus which can obtain dispersion of retardation values with respect to wavelengths.

According to the present invention, a sample having birefringence is held between a polarizer and an analyzer which are maintained in a constant relation of polarization directions to each other. Multiple-wavelength or white measuring light is applied to the sample through the polarizer, so that the light being passed through the sample and transmitted through the analyzer is separated into spectral components by a spectroscope which is provided on the analyzer side. Thus collected are data on dependency of transmitted light intensity on polarization azimuth angles with respect to the measuring light of a plurality of wavelengths. In order to collect such data, the polarizer and the analyzer are relatively rotated with respect to the sample, or a plurality of combinations of such polarizers and analyzers are closely arranged to have different polarization azimuth angles. In order to make measurement with respect to a plurality of wavelengths, measuring light being incident upon the polarizer may be separated into spectral components and wavelength-scanned, in place of separation of the light transmitted through the analyzer.

According to the present invention, further, data on transmitted light intensity with respect to polarization azimuth angles as to measuring light of a plurality of wavelengths are stored in a data memory. When data of a plurality of wavelengths are required for measuring a certain specific sample, therefore, it is possible to fetch required data from the data memory. Further, it is also possible to obtain dispersibility of retardation values of an arbitrary sample with respect to the wavelengths.

Since data can be collected as to a plurality of wavelengths to be stored in the memory, it is possible to quickly select data of an arbitrary wavelength for data processing. Thus, wavelength dispersion of retardation values can be obtained for bringing useful information for basic research, development etc. as to materials.

In addition, it is possible to quickly obtain required data also when data of a plurality of wavelengths are employed for deciding optical degrees for calculating retardation values and the like.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
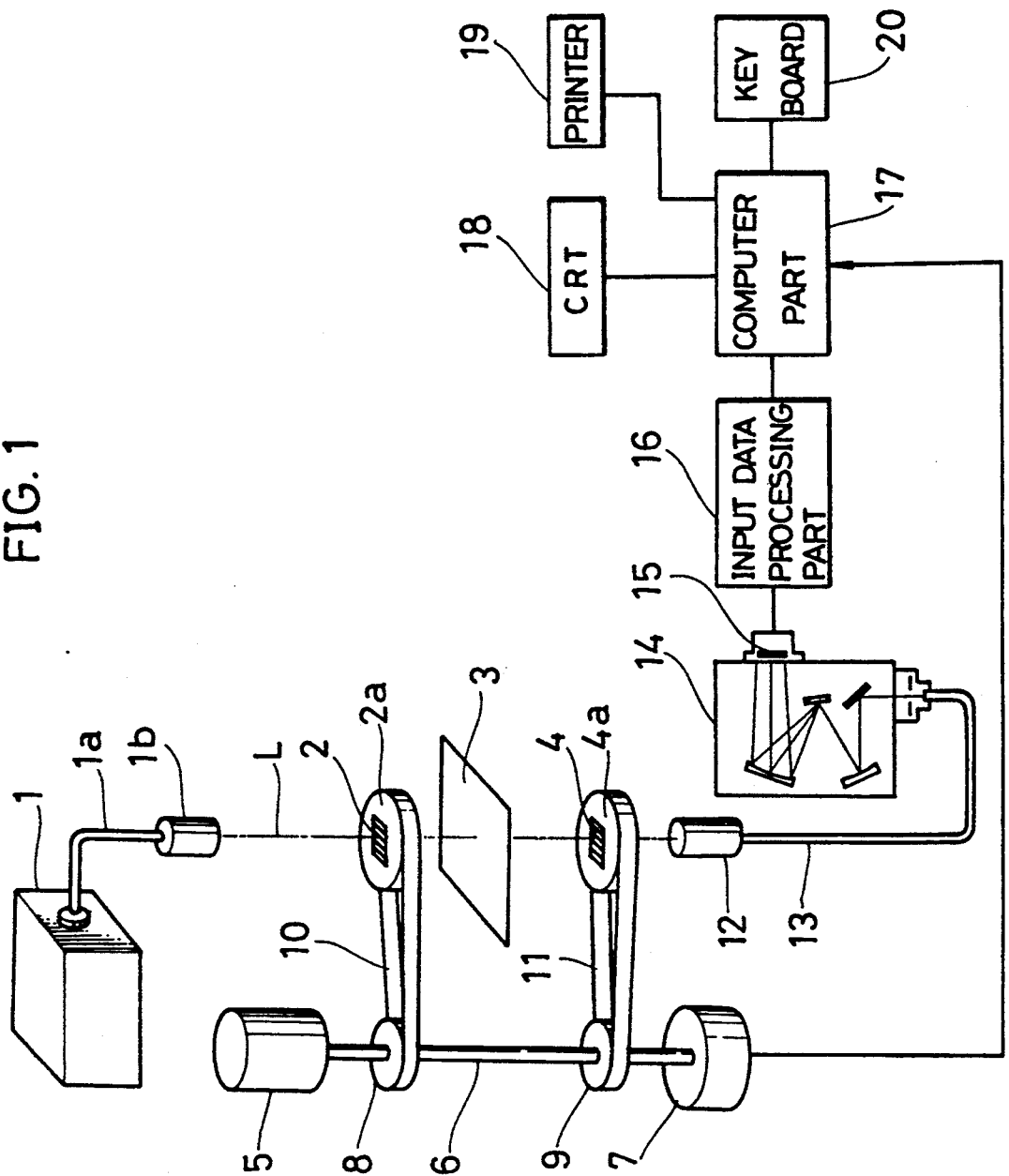
FIG. 1 is a schematic block diagram showing a retardation measuring apparatus according to an embodiment of the present invention.

Referring to FIG. 1, a light source 1 having substantially uniform wavelength distribution over a required waveband is preferably formed by a white light source such as a deuterium lamp or a halogen lamp, for example. Measuring light emitted from the light source 1 is guided by an optical fiber bundle 1a which is provided on its forward end with an outgoing end 1b having an appropriate optical element such as a condenser lens, to be applied to a polarizer 2 as a narrow beam having a proper diameter. The polarizer 2, which is adapted to convert the applied beam into linearly polarized light of a specific polarization direction, is combined with an analyzer 4, which is adapted to transmit a light component of the specific polarization direction in the measuring light being transmitted through a sample 3, in a constant relation of polarization directions such as a parallel nicol relation, for example. The polarizer 2 and the analyzer 4 are held by holding frames 2a and 4a respectively, to be rotatable about an optical axis L of the measuring light. The polarization directions of the polarizer 2 and the analyzer 4 is preferably maintained in the aforementioned parallel relation in order to simplify data processing, although these members may be out of such a parallel nicol relation.

A transmission mechanism is provided in order to rotate the polarizer 2 and the analyzer 4 about the optical axis L while maintaining the same in a constant angle direction. This transmission mechanism is formed by a driving shaft 6, pulleys or belt pulleys 8 and 9 fixed on the driving shaft 6, and belts or wires 10 and 11 coupling the pulleys or belt pulleys 8 and 9 with the outer peripheral portions of the holding frames 2a and 4a, which partially form the transmission mechanism. A motor 5, such as a stepping motor, for example, is coupled to the driving shaft 6, in order to rotate the same. The driving shaft 6 is provided with an encoder 7 for fetching a rotation angle signal of the driving shaft The sample 3, which is in the form of a sheet, having birefringence is held between the polarizer 2 and the analyzer 4.

A spectroscope 14 is provided in order to separate the light being transmitted through the analyzer 4 into spectral components. In order to guide the light being transmitted through the analyzer 4 to the spectroscope 14, an optical fiber bundle 13 having an incident end 12, which is provided with a condenser lens or mirror on its forward end, is connected to the spectroscope 14. The spectroscope 14 comprises a polychromator and a one-dimensional optical sensor 15 such as a one-dimensional CCD for detecting light which is dispersed every wavelength on an outlet imaging surface of the polychromator and photoelectrically converting the same every wavelength. An input data processing part 16 is adapted to amplify detection outputs of the one-dimensional optical sensor 15 for performing processing such as conversion from analog signals to digital signals, and a computer part 17 is adapted to perform various data processing operations on data received from the input data processing part 16. The computer part 17 includes a CPU, a ROM containing a control program for controlling the operation of the overall apparatus, programs for carrying out various arithmetic operations and the like, a RAM for serving as an input/output buffer memory and storing processed data, and the like. The computer part 17 is connected with a CRT device 18 for displaying the processed data, a printer 19 for printing and outputting these data, and keyboard 20 for inputting various data.

The operation of this embodiment is now described. White light (measuring light) emitted from the light source 1 is passed through the optical fiber bundle 1a and applied to the polarizer 2 from the outgoing end 1b. The polarizer 2 and the analyzer 4 are integrally rotated about the optical axis L. A motor control circuit (not shown) outputs control pulses to the motor 5 by a program which is stored in a memory of the computer part 17, to intermittently rotate the polarizer 2 and the analyzer 4 every prescribed small angle, such as 1 degree, for example.

The measuring light being applied to and transmitted through the polarizer 2 is converted to linearly polarized light along a polarization direction responsive to the rotation angle of the polarizer 2, to be incident upon the sample 3. Wavelength components of the light being passed through the sample 3 are out of phase with respect to the incident light, in response to retardation values of the sample 3. Intensity of the measuring light being transmitted through the analyzer 4 is varied with the wavelength components. The light being transmitted through the analyzer 4 is collected by the condenser lens (or mirror) of the incident end 12, and incident upon the spectroscope 14 through the optical fiber bundle 13. The spectroscope 14 disperses the incident polarized light of a specific direction in response to wavelength components so that the light components are received by the one-dimensional optical sensor 15 every wavelength component and converted into electric signals respectively.

Outputs from the optical sensor 15 are amplified by the input data processing part 16 every wavelength, simultaneously or successively A-D converted every wavelength in synchronization with a rotation angle signal generated from the encoder 7, introduced into the computer part 17, stored in the memory and thereafter subjected to required data processing. In more concrete terms, the data on the transmitted light intensity introduced into the computer part 17 are classified, coordinated and stored in the RAM, for example, in relation to measuring wavelengths and polarization rotation angles. Consequently, it is possible to arbitrarily fetch transmitted light intensity data concerning to a required specific measuring wavelength and the polarization rotation angle for forming a chart indicating dependency of the transmitted light intensity with respect to the polarization rotation angle and calculate the retardation value. Further, it is possible to obtain retardation values as to respective wavelengths, obtain dispersion of the retardation values with respect to the wavelengths, and display the same on the CRT or record the same.

Figure 2:
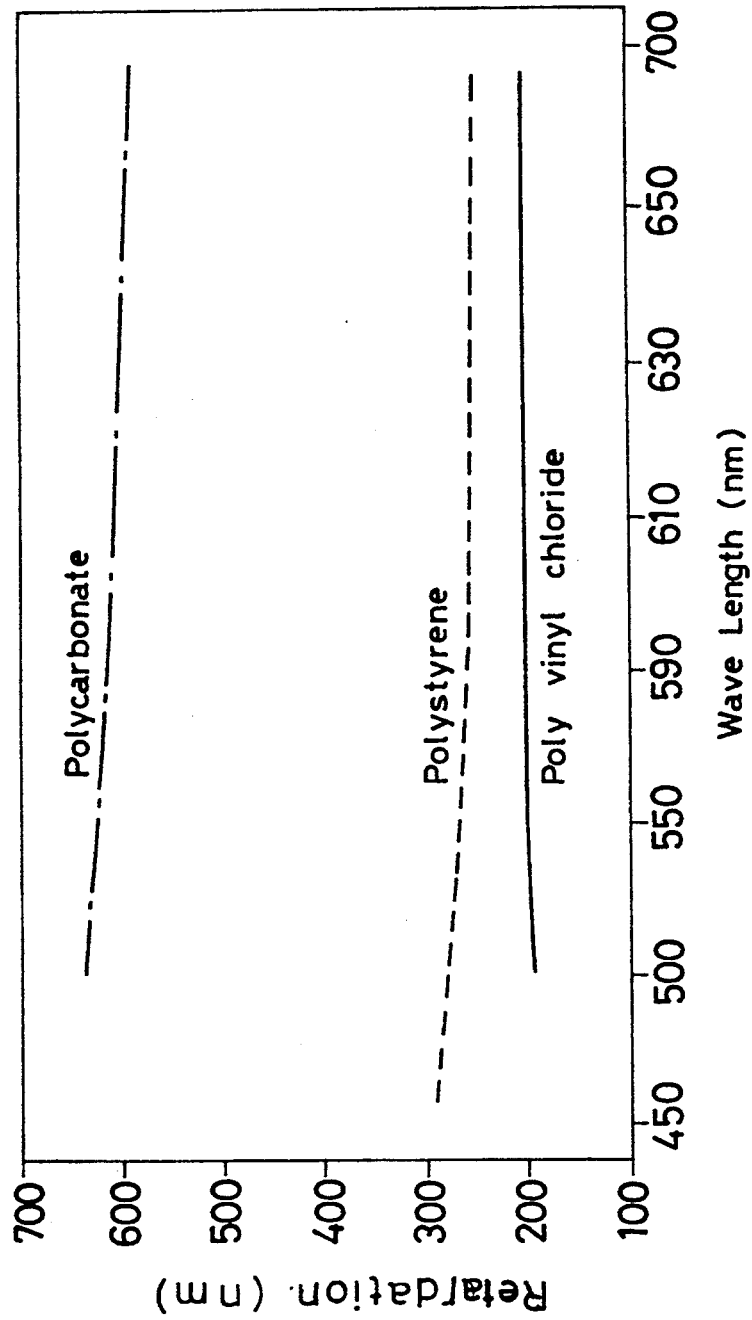
FIG. 2 illustrates exemplary dispersion spectra of retardation with respect to wavelengths obtained according to the present invention.

FIG. 2 illustrates an exemplary recording of dispersion of retardation values with respect to wavelengths obtained in the aforementioned manner.

According to this embodiment, it is possible to complete a measurement for a shorter time because data of a plurality of wavelengths are obtained simultaneously without changing the wavelengths.

Figure 3:
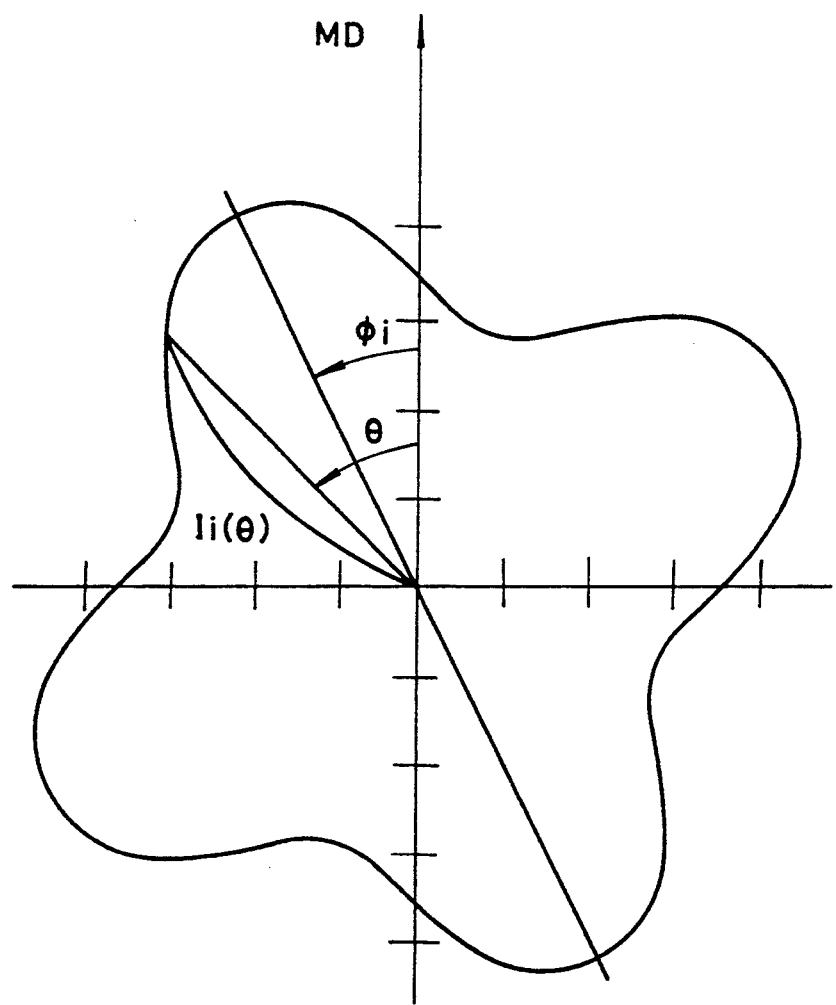
FIG. 3 illustrates distribution of intensity of light transmitted through an analyzer with respect to polarization azimuth angles, as to measuring light of a certain wavelength.
Figure 4:
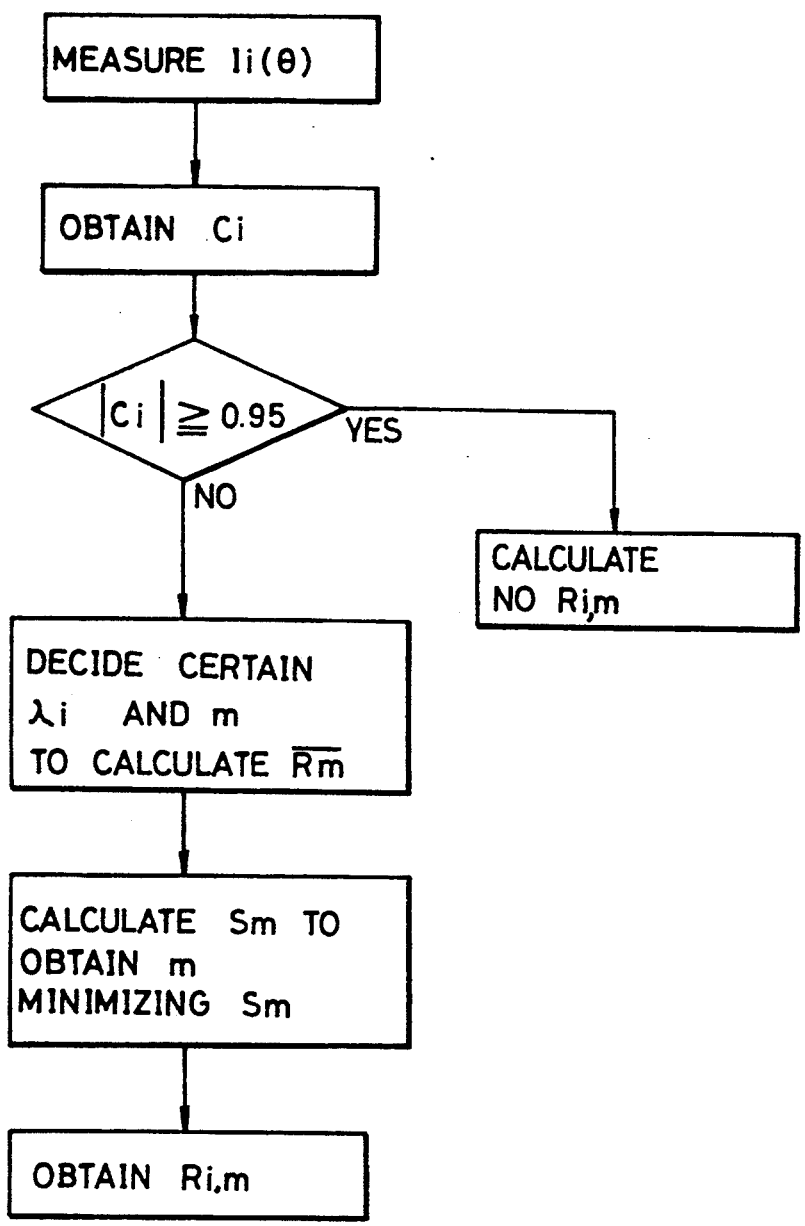
FIG. 4 is a flow chart showing a procedure for deciding an optical degree for deciding retardation values from angle distribution of transmitted light intensity of a plurality of wavelengths.

A method of obtaining retardation values through transmitted light intensity data obtained at a plurality of wavelengths is now described with reference to FIGS. 3 and 4. FIG. 3 illustrates transmitted light intensity $Ii(\theta)$ with respect to measuring light of a certain wavelength $\lambda i$ obtained when a polarizer and an analyzer are maintained in a parallel nicol relation and relatively rotated with respect to a sample which is held therebetween, and FIG. 4 illustrates a procedure for obtaining retardation values.

The transmitted light intensity $Ii(\theta)$ is expressed as follows:
$Ii(\theta) = Ai^2\{ai^2 \cos^4(\theta - \phi i) + \sin^4(\theta - \phi i) + \frac{1}{2} \cdot Ciai \sin^2 2(\theta - \phi i)\} Ci \equiv \cos(2\pi Ri/\lambda i)$ where $\theta$ represents the rotation angle of the polarizer and the analyzer, $\lambda i$ represents the wavelength, $Ai$ represents the amplitude of a linearly polarized wave being transmitted through the analyzer at the wavelength $\lambda i$, $\phi i$ represents the azimuth of the main refractive index of the sample at the wavelength $\lambda i$, $Ri$ represents the retardation value of the sample at the wavelength $\lambda i$, and $\alpha i$ represents the amplitude transmittance ratio at the wavelength $\lambda i$.

From distribution of $Ii(\theta)$ with respect to the polarization rotation angle, the unknown quantities $Ai$, $\alpha i$ and $Ci$ can be obtained as follows:

$$Ai = \sqrt{Ii(\phi i + \pi/2)}$$

$$\alpha i = \sqrt{Ii(\phi i)/Ii(\phi i + \pi/2)}$$

$$Ci = \{4Ii(\phi i + \pi/4) - (\alpha i^2 + 1)Ii(\phi i + \pi/2)\}/2\alpha i Ii(\phi i + \pi/2)$$

when $Ci$ is thus obtained, the retardation value $Ri$, $m$ can be obtained as follows:

$$Ri,m = (\lambda i/2\pi)[\{m-(1-(-1)^m)/2\}\pi - (-1)^m \cos^{-1} Ci] m=1,2,3,\ldots$$

where m represents an optical degree, which can be obtained in the following procedure: First, an upper limit $R_o$ of a measuring range for the retardation value is decided. Assuming that $m_o i$ represents the upper limit of the optical degree with respect to the wavelength $\lambda i$, therefore, $$m_o i = 2R_o/\lambda i$$

It is assumed that $e,ovs/Rm/$ represents the average value of the $n+1$ retardations of optical degree m between certain wavelengths $\lambda i$ and $\lambda i+n$.

$$\overline{Rm} = \sum_{i=i}^{i+n} Ri, m/(n+1)$$

$$m = 1, 2, \ldots, m_o i$$

Then, it is assumed that $Sm$ represents the square sum of difference between $Ri$, $m$ and $\overline{Rm}$.

$$Sm = \sum_{i=i}^{i+n} (Ri, m - \overline{Rm})^2$$

$$m = 1, 2, \ldots, m_o i$$

The retardation value $Ri$, $m$ can be regarded substantially unchanged in the range between the wavelengths $\lambda i$ and $\lambda i+n$ by taking the interval between the wavelengths $\lambda i$ and $\lambda i+n$ sufficiently small as compared with a waveband for measuring dispersion of retardation values. Therefore, the value of m for minimizing the value of $Sm$ is decided as a correct optical degree. When the absolute value of $Ci$ takes a value which is approximate to 1, such that $|Ci| \geq 0.95$, for example, in the procedure for deciding the optical degree m, the wavelength $\lambda i$ is not employed as the wavelength for deciding the optical degree m since the value $Ri$, $m$ corresponding to the current wavelength $\lambda i$ causes a larger error as compared with another range.

Figure 5:
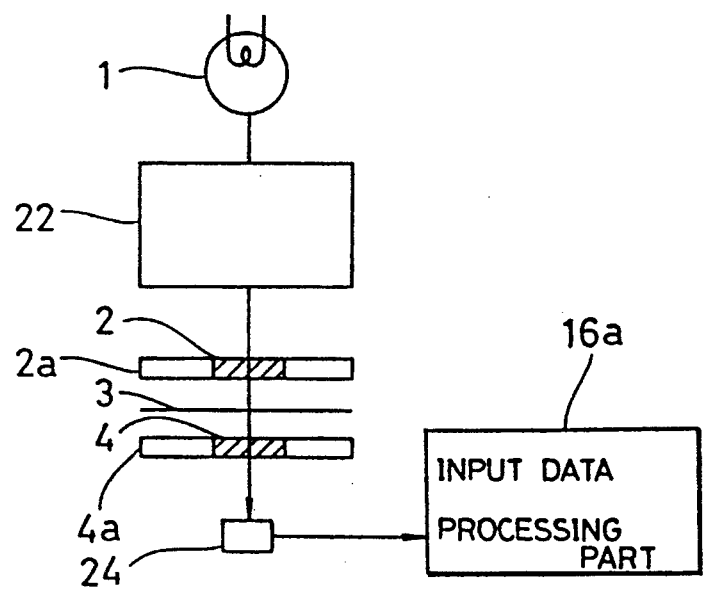
FIG. 5 is a schematic diagram showing an optical system according to another embodiment of the present invention.

FIG. 5 illustrates another embodiment of the present invention.

Referring to FIG. 5, white light emitted from a light source 1 is separated by a spectroscope 22 into spectral components, which in turn are successively applied to a polarizer 2 as monochromatic measuring light components over a plurality of wavelengths. The light components being passed through a sample 3 and transmitted through an analyzer 4 are received by a single optical sensor 24, and incorporated in an input data processing part 16a.

The operation of the embodiment shown in FIG. 5 is described with reference to FIG. 6. The polarizer 2 and the analyzer 4 are maintained in a constant polarization relation and intermittently driven for rotation. When the polarizer 2 and the analyzer 4 are stopped upon rotation at a prescribed small angle, the spectroscope 22 performs wavelength scanning, so that detection signals generated from an optical sensor 24 every wavelength are incorporated in the input data processing part 16a and converted to digital signals. Upon completion of the wavelength scanning, the incorporated data are stored in a memory. Thereafter the polarizer 2 and the analyzer 4 are again rotated at a prescribed angle, to repeat the aforementioned operation. Retardation values are calculated upon full rotation of the polarizer 2 and the analyzer 4.

Figure 6:
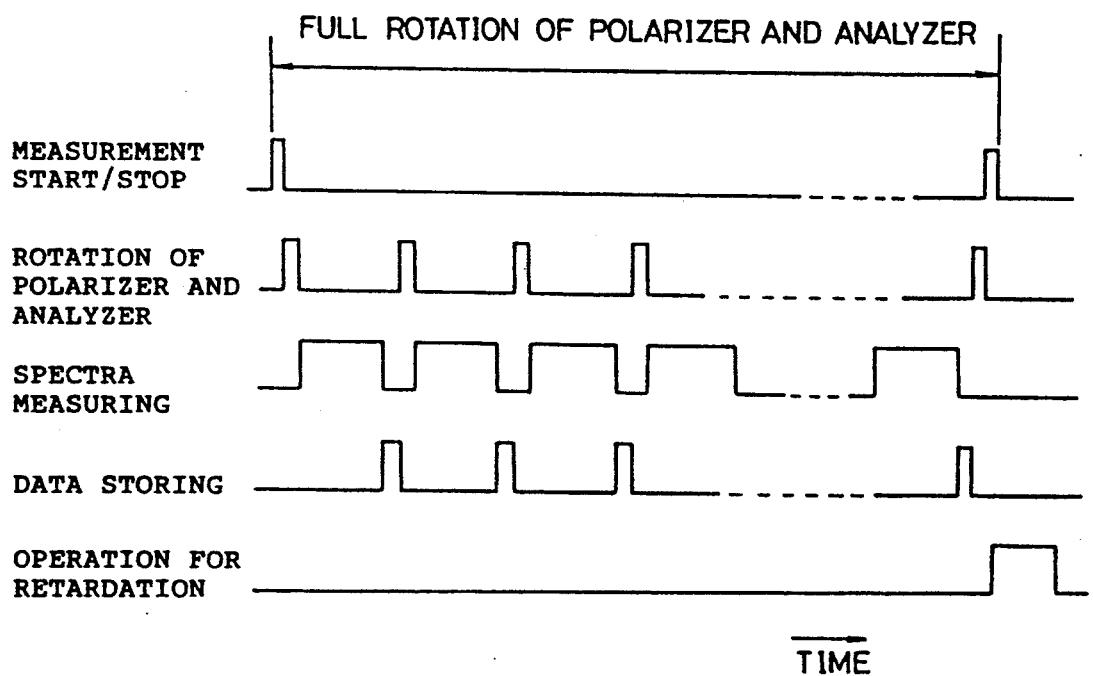
FIG. 6 is an exemplary time chart showing the operation of the present invention.

FIG. 6 is also used for explaining the operation of the embodiment shown in FIG. 1.

The present invention is not restricted to the embodiments. While the polarizer and the analyzer are rotated with respect to the sample for sampling transmitted light intensity data every rotation angle in each embodiment, a plurality of combinations of a polarizer and an analyzer may be arranged to have different polarization azimuth angles, for example, for separating light components being transmitted through the analyzers into spectral components and detect the intensity levels of the transmitted light components as to the respective wavelength components.

The scanning type spectroscope 22 and the single optical sensor 24 used in the embodiment shown in FIG. 5 may be used in the embodiment shown in FIG. 1 in place of the spectroscope 14 and the one-dimensional optical sensor 15.

Although the present invention has been described and illustrated in detail, it is clearly understood that the same is by way of illustration and example only and is not to be taken by way of limitation, the spirit and scope of the present invention being limited only by the terms of the appended claims.

The features disclosed in the foregoing description, in the claims and/or in the accompanying drawings may, both, separately and in any combination thereof, be material for realising the invention in diverse forms thereof.

What is claimed is:

1. A birefringence measuring apparatus, comprising:
   a combination of a polarizer and an analyzer being maintained in a constant relation of polarization directions relative to each other;
   a mechanism for holding a sample having birefringence between said polarizer and said analyzer;
   a measuring light optical system for applying a multiple-wavelength light to said sample through said polarizer;
   a spectroscope for separating said light being passed through said sample and transmitted through said analyzer into spectral components for detecting transmitted light intensity values as to a plurality of wavelengths, said transmitted light intensity values being obtained at a plurality of wavelengths as to a plurality of polarization azimuth angles of said polarizer and said analyzer; and means for deciding on employment of said transmitted light intensity values in a case where an absolute value of Ci takes on a value smaller than a predetermined value, wherein $$Ci=[4Ii(\phi i+\pi/4)-(\alpha i^2+1)Ii(\phi i+\pi/2)]/2\alpha i Ii(\phi i+\pi/2),$$

$Ii(\phi i+\pi/4)$ and $Ii(\phi i+\pi/2)$ represent said transmitted light intensity values as to a certain wavelength $\lambda i$ at rotation angles of $(\phi i+\pi/4)$ and $(\phi i+\pi/2)$ of said polarizer and said analyzer respectively when said polarizer and said analyzer are maintained in a parallel nicol relation, $\phi i$ represents the azimuth of the main refractive index of said sample at the wavelength $\lambda i$, and $\alpha i$ represents the amplitude transmittance ratio at the wavelength $\lambda i$.

2. A birefringence measuring apparatus, comprising:
a combination of a polarizer and an analyzer being maintained in a constant relation of polarization directions relative to each other;
a mechanism for holding a sample having birefringence between said polarizer and said analyzer;
a measuring light optical system for separating light received from a light source into spectral components for applying wavelength-scanned monochromatic measuring light components to said sample over a plurality of wavelengths through said polarizer;
an optical sensor for detecting said measuring light components being passed through said sample and transmitted through said analyzer, wherein transmitted light intensity values of a plurality of wavelengths are obtained at a plurality of polarization azimuth angles of said polarizer and said analyzer; and
means for deciding on employment of said transmitted light intensity values in a case where an absolute value of Ci takes on a value smaller than a predetermined value, wherein $$Ci=[4Ii(\phi i+\pi/4)-(\alpha i^2+1)Ii(\phi i+\pi/2)]/2\alpha i Ii(\phi i+\pi/2),$$

$Ii(\phi i+\pi/4)$ and $Ii(\phi i+\pi/2)$ represent said transmitted light intensity values as to a certain wavelength $\lambda i$ at rotation angles of $(\phi i+\pi/4)$ and $(\phi i+\pi/2)$ of said polarizer and said analyzer respectively when said polarizer and said analyzer are maintained in a parallel nicol relation, $\phi i$ represents the azimuth of the main refractive index of said sample at the wavelength $\lambda i$, and $\alpha i$ represents the amplitude transmittance ratio at the wavelength $\lambda i$.

3. A birefringence measuring apparatus, comprising:
a combination of a polarizer and an analyzer being maintained in a constant relation of polarization directions relative to each other;
a mechanism for holding a sample having birefringence between said polarizer and said analyzer;
a measuring light optical system for applying a multiple-wavelength light to said sample through said polarizer;
a spectroscope for separating said measuring light being passed through said sample and transmitted through said analyzer into spectral components for detecting transmitted light intensity values as to a plurality of wavelengths;
storage means for storing said transmitted light intensity values as to a plurality of polarization azimuth angles of said polarizer and said analyzer;
an arithmetic part for calling transmitted light intensity data for polarization azimuth angles as to a plurality of wavelengths from said storage means for calculating retardation values with respect to a plurality of wavelengths, thereby measuring dispersibility of said retardation values with respect to wavelengths; and
means for deciding on employment of said transmitted light intensity values in a case where an absolute value of Ci takes on a value smaller than a predetermined value, wherein $$Ci=[4Ii(\phi i+\pi/4)-(\alpha i^2+1)Ii(\phi i+\pi/2)]/2\alpha i Ii(\phi i+\pi/2),$$

$Ii(\phi i+\pi/4)$ and $Ii(\phi i+\pi/2)$ represent said transmitted light intensity values as to a certain wavelength $\lambda i$ at rotation angles of $(\phi i+\pi/4)$ and $(\phi i+\pi/2)$ of said polarizer and said analyzer respectively when said polarizer and said analyzer are maintained in a parallel nicol relation, $\phi i$ represents the azimuth of the main refractive index of said sample at the wavelength $\lambda i$, and $\alpha i$ represents the amplitude transmittance ratio at the wavelength $\lambda i$.

4. A retardation measuring apparatus, comprising:
a combination of a polarizer and an analyzer being maintained in a constant relation of polarization directions relative to each other;
a mechanism for holding a sample having birefringence between said polarizer and said analyzer;
a measuring light optical system for separating light received from a light source into spectral components for applying wavelength-scanned monochromatic measuring light components to said sample over a plurality of wavelengths through said polarizer;
an optical sensor for detecting said light being passed through said sample and transmitted through said analyzer;
storage means for storing said transmitted light intensity values as to a plurality of wavelengths as to a plurality of polarization azimuth angles of said polarizer and said analyzer;
an arithmetic part for calling transmitted light intensity data for polarization azimuth angles as to a plurality of wavelengths from said storage means for calculating retardation values with respect to a plurality of wavelengths, thereby measuring dispersibility of said retardation values with respect to wavelengths; and
means for deciding on employment of said transmitted light intensity values in a case where an absolute value of Ci takes on a value smaller than a predetermined value, wherein $$Ci=[4Ii(\phi i+\pi/4)-(\alpha i^2+1)Ii(\phi i+\pi/2)]/2\alpha i Ii(\phi i+\pi/2),$$

$Ii(\phi i+\pi/4)$ and $Ii(\phi i+\pi/2)$ represent said transmitted light intensity values as to a certain wavelength $\lambda i$ at rotation angles of $(\phi i+\pi/4)$ and $(\phi i+\pi/2)$ of said polarizer and said analyzer respectively when said polarizer and said analyzer are maintained in a parallel nicol relation, $\phi i$ represents the azimuth of the main refractive index of said sample at the wavelength $\lambda i$, and $\alpha i$ represents the amplitude transmittance ratio at the wavelength $\lambda i$.

* * * * *